United States Patent [19]

Nichols

[11] Patent Number: 4,460,361
[45] Date of Patent: Jul. 17, 1984

[54] VACUUM PORT CONNECTOR ASSEMBLY ON FLUID COLLECTION APPARATUS

[75] Inventor: Robert L. Nichols, Jacksonville, Tex.

[73] Assignee: American Hospital Supply Corp., Evanston, Ill.

[21] Appl. No.: 435,384

[22] Filed: Oct. 20, 1982

Related U.S. Application Data

[63] Continuation of Ser. No. 173,885, Jul. 31, 1980, abandoned.

[51] Int. Cl.³ .............................................. A61M 1/00
[52] U.S. Cl. .................................................... 604/319
[58] Field of Search ............................... 128/276–278, 128/760; 285/DIG. 15; 604/35, 48, 93, 319–321, 323, 326, 327; 132/205; 433/97

[56] References Cited

U.S. PATENT DOCUMENTS

| | | | |
|---|---|---|---|
| 2,394,363 | 2/1946 | Bynoe | 285/DIG. 15 |
| 3,713,444 | 1/1973 | Bridgman | 604/320 |
| 3,866,608 | 2/1975 | Reynolds et al. | 604/319 |
| 3,983,872 | 10/1976 | Nehring | 128/278 |
| 3,989,046 | 11/1976 | Pannier, Jr. et al. | 604/319 |
| 4,211,439 | 7/1980 | Moldestad | 285/DIG. 15 |
| 4,296,748 | 10/1981 | Kurtz et al. | 604/319 |
| 4,321,922 | 3/1982 | Deaton | 604/35 |

OTHER PUBLICATIONS

Catalog Cut "Receptal A.T.S.", Sorenson Research Co., Salt Lake City, Utah 84115, Jan. 1978.
Catalog Cut "Fisher Scientific Co.", Catalog 65, 1964.

Primary Examiner—John D. Yasko
Assistant Examiner—J. L. Kruter
Attorney, Agent, or Firm—Jerry W. Mills; Jerry R. Selinger; Greg M. Howison

[57] ABSTRACT

An improved vacuum attachment assembly for suction apparatus is provided. The invention includes a vacuum line coupling system that is incompatible with the inlet port such that inadvertent attachment of the vacuum line to the inlet port is impossible. The vacuum connection system further includes a permanently attached tee and vacuum leader line for parallel connection of the vacuum source to the interior and exterior of a liner disposed within the apparatus. The improved vacuum attachment system allows easy disconnection and reconnection of the vacuum source.

1 Claim, 2 Drawing Figures

VACUUM PORT CONNECTOR ASSEMBLY ON FLUID COLLECTION APPARATUS

This is a continuation of application Ser. No. 173,885, filed July 31, 1980, now abandoned.

TECHNICAL FIELD

The present invention relates to medical suction apparatus, and more particularly relates to an assembly for connecting a vacuum line thereto.

BACKGROUND ART

Medical suction apparatus has long been used in hospitals to remove fluids from patients during various medical procedures. An example of such apparatus is shown in U.S. Pat. No. 4,321,922 entitled "MEDICAL RECEPTACLE WITH DISPOSABLE LINER ASSEMBLY," and issued Mar. 30, 1982. Such apparatus usually includes a canister having a vacuum-tight cover in which several ports are provided through which fluids are introduced or evacuated from the canister. These ports are usually fitted with connection apparatus for connecting various hoses or tubes to the apparatus. A typical device in this art has a vacuum tube for applying vacuum to the canister and one or more inlet tubes through which fluids and debris from the patient enter the canister.

A drawback of prior receptacles is the interchangeability of the tubes with either the inlet port or the vacuum port. Because of this interchangeability, it may be possible to misconnect the vacuum and inlet tubes by connecting an inlet tube to the vacuum port and the vacuum tube to an inlet port. If the tubes are crossed in this fashion, fluid and debris enter the vacuum port and vacuum is applied to the inlet port.

This connection mistake could have several undesirable consequences. The suction apparatus could initially function properly and the mistake in connecting the hoses not be immediately apparent. After a short interval, however, debris entering the vacuum port could tend to clog a filter that is often incorporated in the vacuum port. An example of such a filter is shown in U.S. Pat. No. 4,228,798 entitled "SUCTION RECEPTACLE WITH HYGROSCOPIC FILTER", and issued Oct. 21, 1980. Such filters permit the flow of air exiting the container through the vacuum port in normal use but may clog quickly when through accidental misconnection body fluids and debris are passed through the filter. Of course, in addition to clogging of the filter, the filter is not able to prevent passage of aerosol and bacteria into vacuum lines of the hospital.

Another undesirable consequence of an accidental reversing of the vacuum and inlet lines is the bypassing of any shut-off valve which may be associated with the vacuum port. A valve of this type, illustrated in U.S. Pat. No. 4,321,923 entitled "LOW PROFILE SHUT-OFF VALVE FOR MEDICAL SUCTION APPARATUS," issued Mar. 30, 1982, interrupts suction when the fluid level in the container approaches the cover of the container. Within the valve a float raises and interrupts the flow of air from the container into the vacuum line thus preventing the flow of fluids into the vacuum line. It can be seen that if the inlet line and vacuum line are reversed, no valve is disposed between the container and the vacuum line since such valves are not usually incorporated with inlet ports. When the container is full, fluids could then flow into the vacuum system causing highly deleterious contamination and possible malfunction.

Suction apparatus having a disposable liner within a rigid canister often utilize special vacuum connections so that in operation the interior and exterior of the liner are at approximately the same vacuum level. Thus it has been necessary to provide vacuum connections in parallel, one connection through the side of the rigid canister such that vacuum is applied to the exterior of the inner liner and another connection through the cover of the canister such that vacuum is applied to the interior of the inner liner. In prior apparatus this parallel connection was accomplished using a tee or "Y" connection splitting the vacuum line into two branches. Each branch is then attached to the canister using short pieces of hose. The tee or "Y" connector and the two relatively short pieces of hose are specialized apparatus that have to be on hand to enable operation of the device. The extra hoses complicate the working environment of the apparatus and detract from the appearance of the apparatus. Thus, the added complexity caused by this additional apparatus is a drawback of prior receptacles incorporating disposable inner liners.

DISCLOSURE OF THE INVENTION

The present invention provides an improved vacuum line connecting system for use with suction apparatus which substantially improves or eliminates the aforesaid deficiencies in prior art vacuum systems. In preferred form, specialized coupling apparatus for connecting the vacuum line to the vacuum port is provided, making inadvertent cross-connection of an inlet line to a vacuum port and vacuum line to an inlet port impossible. In another preferred aspect of the invention, an improved vacuum line connection system is provided for use with suction apparatus having a rigid outer canister and an inner liner. To equalize the pressure differential across the exterior and interior of the inner liner, a vacuum tee connection is permanently attached to the rigid canister and one branch of the tee communicates with the interior of the canister. On another branch of the tee a short, flexible and autoclavable vacuum leader line is permanently attached and made a permanent part of the apparatus. The other end of the leader line is fitted to removably attach to the vacuum port of the apparatus. Other aspects and advantages will be become apparent hereinafter.

BRIEF DESCRIPTION OF THE DRAWINGS

A more complete understanding of the invention and its advantages will be apparent from the Detailed Description taken in conjunction with the accompanying Drawings in which.

DETAILED DESCRIPTION

Figure 1:
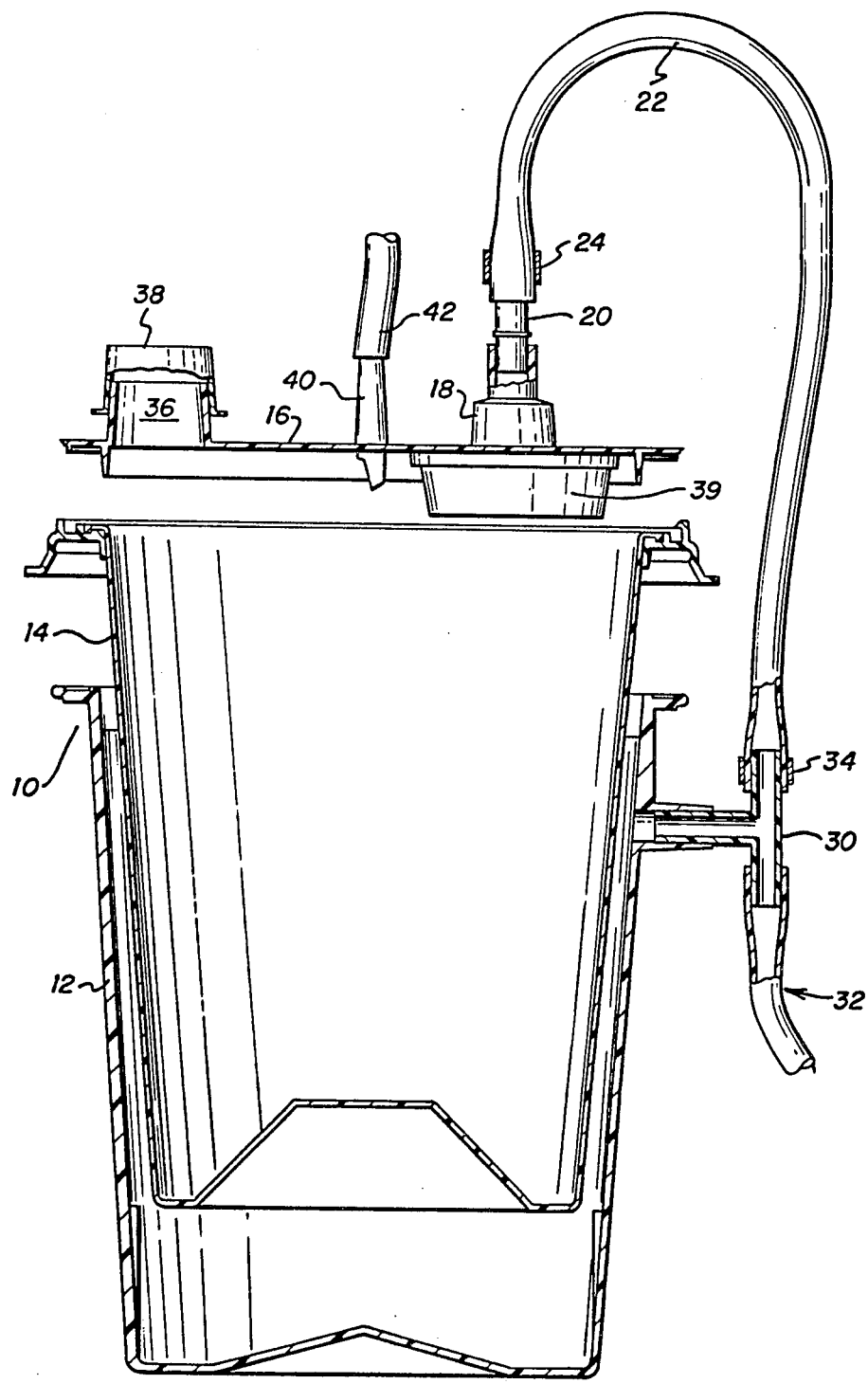
FIG. 1 is an exploded sectional view of a suction apparatus constructed in accordance with the invention having the vacuum leader line connected for operation.

Referring initially to FIG. 1, receptacle 10 receives fluids and debris from the exterior of the receptacle. The receptacle 10 includes a rigid outer canister 12 which supports a disposable inner liner 14 therein. A cover 16 is fitted over the receptacle 10 and includes a female-type vacuum port 18 for connection to a vacuum source through a male-type fitting 20 and vacuum leader line 22. Fitting 20 is permanently attached to vacuum leader line 22 by tubing clamp 24. The canister 12 has permanently attached thereto a vacuum tee 30 for parallel connection to a vacuum source through tube 32. Vacuum tee 30 communicates through the side wall of canister 12. Vacuum leader line 22 is permanently attached to vacuum tee 30 by tubing clamp 34. Cover 16 further includes a pour spout 36 with a lid 38 to enable the contents of canister 12 to be easily emptied. A shut-off valve 39 is associated with vacuum port 18. The cover 16 also has an inlet port 40 for receiving fluid from the exterior of the receptacle through an inlet line 42.

For more detail regarding the construction and operation of the illustrated vacuum system, reference is made to copending patent application Ser. No. 113,620, entitled MEDICAL RECEPTACLE WITH DISPOSABLE LINER ASSEMBLY, filed Jan. 21, 1980, now U.S. Pat. No. 4,321,922, issued Mar. 30, 1982.

Leader line 22 is formed from a heavy duty plastic which can be used a plurality of times and which can withstand autoclave high-temperature steam cleaning. Tube 32 and inlet line 42 comprise any suitable type of plastic tubing normally used in hospital suction environments.

Figure 2:
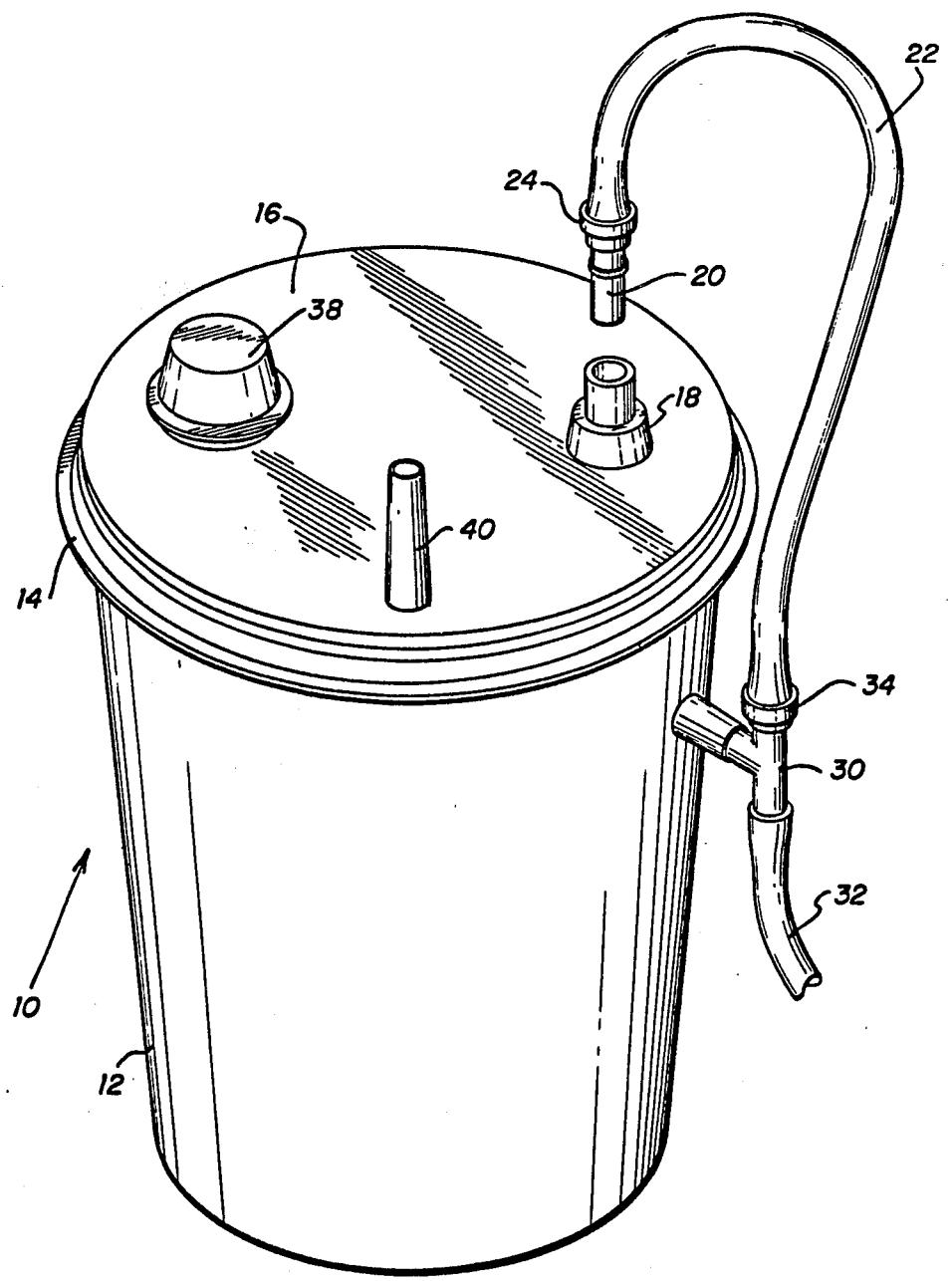
FIG. 2 is a perspective view of FIG. 1 showing the vacuum leader line disconnected.

In FIGS. 1 and 2, like numerals are used to designate like and corresponding elements. FIG. 2 shows receptacle 10 having inlet port 40 disconnected and vacuum leader line 22 disconnected from port 18.

In operation, the tube 32 is connected to the hospital vacuum source and line 42 is directed to the patient area in order to suction up patient fluid and debris. The patient fluids are drawn through inlet line 42 and inlet port 40 by the vacuum within the liner 14 and collected within liner 14. Vacuum is applied to the interior of the canister 12 and liner 14 through leader line 22, fitting 20 and vacuum port 18. Vacuum port 18 has a built-up base to accommodate therein a filter for preventing passage of aerosol and bacteria into vacuum leader line 22. Vacuum tee 30 communicates with the interior of outer canister 12 such that vacuum is applied to the exterior of inner liner 14 to tend to equalize the pressure differential across liner 14.

Fitting 20 and vacuum port 18 are constructed such that a snug and vacuum-tight seal is made when fitting 20 is inserted into vacuum port 18. However, when removal of cover 16 and/or inner liner 14 is desired, leader line 22 and fitting 20 may be easily disconnected from vacuum port 18 by a slight pull. Reconnection is likewise made easy especially since the leader line 22 is permanently attached to canister 12 by tee 30.

Inlet port 40 is fitted with a male-type connection sized such that inlet line 42 may be slipped over the connection, thereby completing a snug and vacuum-tight seal under normal operating vacuums. In contrast, vacuum port 18 is constructed such that a female-type connection is formed on cover 16 of the apparatus. The special fitting 20 attached to vacuum leader line 22 is constructed and sized so that attachment to the male-type inlet port 40 is impossible. Likewise, it is not possible to connect line 42 within port 18. Thus it can be seen that Applicant's invention makes crossing of the connections of the inlet and vacuum lines impossible.

While this aspect of the invention has been described in conjunction with a system having a permanent outer canister and a disposable inner liner, it will be understood that the invention may also be used with conventional suction devices including only a canister and a lid with a vacuum port and a fluid inlet port.

Permanently attached vacuum tee 30 and leader line 22 make the hookup to the vacuum source a matter of attaching vacuum line 32 to tee 30. Thus, the requisite parallel connection is established through the single connection of line 32. Since all the connection equipment is permanently attached to the apparatus, the deployment of the device is greatly simplified. Hospital inventory and purchasing procedures are likewise made simpler by the self-contained nature of the improved apparatus. Applicant's connector assembly reduces the possibility that the various hoses will entangle and otherwise interfere with ongoing procedures in the operating room.

While one embodiment of the present invention has been described in detail herein and shown in the accompanying drawings, it will be evident that various further modifications are possible without departing from the scope of the invention. It will be understood that medical suction apparatus is shown as the environment of the invention for purposes of illustration only. The invention is adaptable to suction apparatus of all types.

I claim:

1. A suction apparatus for suctioning and collecting fluid from a patient comprising:
    a rigid outer canister having an annular rim defining an upwardly opening mouth;
    a disposable semi-rigid inner container having an annular lip extending laterally from said container sidewall and overlying a portion of said canister rim, said container removably disposed within said canister and supported from the top of said canister with a space between the sidewalls of said canister and said container;
    a removable cover for said canister and container having formed therein an inlet port for receiving fluid from the body of a patient, and a vacuum port for effecting a vacuum within said container for drawing fluid through said inlet port for collection in said container;
    an inlet line;
    a vacuum line;
    a tee connection attached directly to the rigid outer canister and communicating with the interior of the rigid outer canister to allow easy disconnection and reconnection of the vacuum line to the vacuum source;
    a flexible autoclavable vacuum leader line having first and second ends and having a length for extending between said tee connection and said vacuum port, said tee connection and said vacuum port, said first end being permanently attached to said tee connection and said second end having detachable vacuum coupling means for attaching said second end to the vacuum port, such that a vacuum applied to said tee from the vacuum line is applied to the exterior and interior of the inner liner;
    said vacuum coupling means including a male-type connector attached to said second end of said vacuum leader line and said vacuum port including a female-type connector, said male connector being dimensioned to interfit with said female-type connector and being inoperable to couple said vacuum leader line to said inlet port; and
    inlet coupling means for attaching the inlet line to the inlet port, said inlet coupling means being inoperable to couple the inlet line to the vacuum port, said inlet coupling means being readily distinguishable from said vacuum coupling means such that attempts to miscouple are minimized.

* * * * *